(12) United States Patent
Martin

(10) Patent No.: US 6,186,996 B1
(45) Date of Patent: *Feb. 13, 2001

(54) DISPOSABLE ABSORBENT SANITARY ARTICLE

(75) Inventor: Françoise Martin, la Madeleine (FR)

(73) Assignee: Peaudouce, Linselles (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/578,679

(22) PCT Filed: Jul. 8, 1994

(86) PCT No.: PCT/FR94/00856

§ 371 Date: Jan. 4, 1996

§ 102(e) Date: Jan. 4, 1996

(87) PCT Pub. No.: WO95/01768

PCT Pub. Date: Jan. 19, 1995

(30) Foreign Application Priority Data

Jul. 9, 1993 (FR) .................................................. 93 08723

(51) Int. Cl.[7] .................................................. A61F 13/15
(52) U.S. Cl. ............................... 604/385.19; 604/385.24; 604/385.27; 604/385.28
(58) Field of Search ............................. 604/385.1, 385.2, 604/386, 387, 373, 378, 385.01, 385.19, 385.24, 385.27, 385.28

(56) References Cited

U.S. PATENT DOCUMENTS

| 4,662,877 | 5/1987 | Williams . | |
|---|---|---|---|
| 4,695,278 | * 9/1987 | Lawson | 604/385.2 |
| 4,846,825 | 7/1989 | Enloe et al. . | |
| 5,542,941 | * 8/1996 | Morita | 604/385.7 |

FOREIGN PATENT DOCUMENTS

| 0190881 | 8/1986 | (EP) . | |
|---|---|---|---|
| 0391476 | 10/1990 | (EP) . | |
| 0371871 | 6/1990 | (FR) . | |
| 2699613 | * 7/1994 | (FR) | 601/385.2 |
| 2161059 | 1/1986 | (GB) . | |
| 2-274250 | * 11/1990 | (JP) . | |
| 2271863 | * 11/1990 | (JP) . | |
| 3-186261 | * 8/1991 | (JP) . | |
| 3-186262 | * 8/1991 | (JP) . | |
| 3207358 | * 9/1991 | (JP) . | |
| 4152947 | * 5/1992 | (JP) . | |
| 4-322646 | * 11/1992 | (JP) | 604/385.2 |
| 5-42180 | * 2/1993 | (JP) | 604/385.1 |
| 5-42181 | * 2/1993 | (JP) | 604/385.1 |
| 5-49658 | * 3/1993 | (JP) | 604/385.2 |

OTHER PUBLICATIONS

Translation of 2271863, Japan.*
Translation of 4152947, Japan.*

* cited by examiner

*Primary Examiner*—John G. Weiss
*Assistant Examiner*—K. M. Reichle
(74) *Attorney, Agent, or Firm*—Burns, Doane, Swecker & Mathis, L.L.P.

(57) ABSTRACT

The disposable absorbent sanitary article includes an absorbent pad placed between a liquid impervious external backing sheet and a hydrophobic internal covering sheet provided with a central opening extending over the absorbent pad. A first set of elastic members is fixed to the backing sheet and to the covering sheet along external edges thereof at least in a crotch area thereof and a second set of elastic members is fixed to the covering sheet along longitudinal edges of the central opening. Two hydrophobic flaps are each realized by fixing a first longitudinal edge of a strip of hydrophobic material close to an external longitudinal edge of the absorbent pad, and a second longitudinal edge to a lower face of the covering sheet close to the elastic members of the second set.

10 Claims, 3 Drawing Sheets

FIG_1

DISPOSABLE ABSORBENT SANITARY ARTICLE

BACKGROUND OF THE INVENTION

The present invention relates to a disposable absorbent sanitary article, such as a disposable diaper for infants or for incontinent adults, comprising an absorbent pad, which is placed on a liquid impervious external backing sheet. More particularly, the invention relates to an improved sanitary article providing a very good tightness in the area of the wearer's thighs, thereby avoiding any risk of urine or faeces leakage along the wearer's legs.

Numerous arrangements have already been proposed in order to achieve such a tightness. A first one consisted in placing elastic elements in the crotch area in order to hold the article to some extent around the wearer's legs. The sanitary article comprises, in the longitudinal direction, a central part which corresponds to the crotch area and two end parts, one being a front part and the other a rear part, which correspond to the zones of the article as positioned and fixed around the wearer's waist. The elastic elements in question are fixed longitudinally along the two external edges of the backing sheet at least in the central part.

However, this first arrangement has proved insufficient insofar as the holding force which is exerted on the wearer's leg is necessarily limited and, in addition, wrinkles are created which generate leaks.

In another arrangement, it has already been proposed, in addition to the elastic elements in the crotch, to provide longitudinal flaps designed to form a barrier against transversal diffusion of faeces. Such flaps are for example described in document GB 2 161 059, in which preferably, each flap is formed by folding over a liquid-permeable protection sheet, which extends over the absorbent pad and which has the same outer shape as the liquid-permeable backing sheet. The barrier effect is achieved notably by interposing inside the folded sheet forming flap, an elastic element which is meant to pull the flap up when the sanitary article is positioned on the wearer.

Another arrangement, described in document U.S. Pat. No. 4,662,877 consists in placing on top of the absorbent pad and the impervious backing sheet, a hydrophobic covering sheet which is fixed to the backing sheet in such a way as to form a sandwich structure. The covering sheet has an opening in the crotch area and is provided with elastic elements fixed along the longitudinal edges of said opening, in a stretched condition such that they tend to pull up said longitudinal edges when the article is in position on the wearer.

Thus, there is obtained an improved barrier effect compared to document GB-2 161 059 due not only to the presence of the longitudinal flaps but also to the presence of the covering sheet on the outermost portions of the absorbent pad which provides a certain transverse protection.

Yet, despite its particularly favorable structure, the sanitary article according to document U.S. Pat. No. 4,662,877 does not provide perfect tightness, as would be expected. Indeed, even if the faeces are concentrated in the inside pouch which opens into the opening of the covering sheet, the fact nevertheless remains that when the wearer remains in the seating position, this causes a migration of liquid beyond the covering sheet and the elastic elements in the crotch area.

It is an object of the present invention to design a sanitary article which overcomes the aforesaid disadvantage. This article is, as conventionally known from document U.S. Pat. No. 4,662,877, a disposable absorbent sanitary article, such as a diaper, which comprises an absorbent pad placed between a liquid impervious external backing sheet and a hydrophobic covering sheet, both sheets having the same shape and defining, in the longitudinal direction, a central part which corresponds to the crotch area and two end parts, one being a front part and the other a rear part, which correspond to the zones of the article as positioned and fixed around the wearer's waist. The backing sheet and the covering sheet are joined together at least along their periphery and the covering sheet comprises a central opening which extends above the absorbent pad; moreover, the sanitary article comprises sets of elastic elements, disposed symmetrically with respect to the article longitudinal axis: a first set, called the crotch set, is fixed to the backing sheet and to the covering sheet along the longitudinal edges thereof, at least in the central part, and the second set is fixed to the covering sheet along the longitudinal edges of the central opening.

SUMMARY OF THE INVENTION

As is typical, the sanitary article according to the invention comprises a set of two hydrophobic flaps, symmetrically arranged with respect to the article longitudinal axis, each flap being made of a strip of hydrophobic material which may be impervious to liquids, if necessary. A first of the two longitudinal edges of said strip is fixed close to the external longitudinal edge of the absorbent pad, at least in the crotch area, and the other, on the lower face of the covering sheet close to the elastic elements of the second set. A double barrier effect is thus obtained, said effect being implemented solely via the second set of elastic elements. Indeed, said set makes it possible to pull up not only the two lateral straps of the covering sheet situated between the central opening and the first set of elastic elements, but also the two hydrophobic flaps. Thus, as in document U.S. Pat. No. 4,662,877, an inside pouch is obtained which opens into the opening of the covering sheet, but said pouch is defined internally by the two hydrophobic flaps and externally by the two lateral straps of the covering sheet. It is the presence of this double barrier which ensures the improved tightness.

The absorbent pad is generally covered with a liquid-permeable protection sheet. Preferably, according to the invention, said protection sheet has a width which is greater than that of the pad, so as to define one central strip, which is permeable to liquids, and two lateral strips which are not permeable to liquids but which are hydrophobic and, if appropriate, impermeable to liquids; moreover, said central strip is fixed longitudinally close to the two longitudinal external edges of the absorbent pad such that said two lateral strips constitute the set of two hydrophobic flaps of the invention. This particular arrangement simplifies the production of the article according to the invention since in that case, production of the two longitudinal flaps does not require any additional components.

Preferably, each lateral strip of the protection sheet comprises a longitudinal fold; the corresponding folding line is fixed longitudinally on the impervious backing sheet along the absorbent pad and externally thereto, at least in the crotch area; the two sides of the longitudinal fold are fixed together at the level of the line along which the protection sheet is fixed to the absorbent pad, and throughout the length of this line.

The object of this particular embodiment is to improve the liquid-tightness of the sanitary article, hence to eliminate all risks of urine leaks which could possibly occur at the level of the absorbent pad along the impervious backing sheet. This is obtained thanks to the longitudinal fold of double thickness, which forms a double barrier against possible migrations of liquid coming from the absorbent pad.

Advantageously, a third set of elastic elements is fixed longitudinally to the covering sheet between the line along which the flap is fixed to said covering sheet and the first set of elastic elements. The use of such a third set of elastic elements contributes to laterally form, along the absorbent pad, two tunnels capable of acting as absorbing reservoirs. In the case where the hydrophobic flaps are made of a gas-permeable material, they constitute ventilation tunnels permitting a gaseous exchange between the inside and the outside of the sanitary article, hence the progressive elimination of the humidity present in the inside pouch.

BRIEF DESCRIPTION OF THE DRAWINGS

The present invention will be more readily understood on reading the description given hereafter of examples of embodiments of a diaper having a covering sheet and a protection sheet forming flap, illustrated in the accompanying drawings, in which.

PREFERRED EMBODIMENTS OF THE INVENTION

Figure 1:
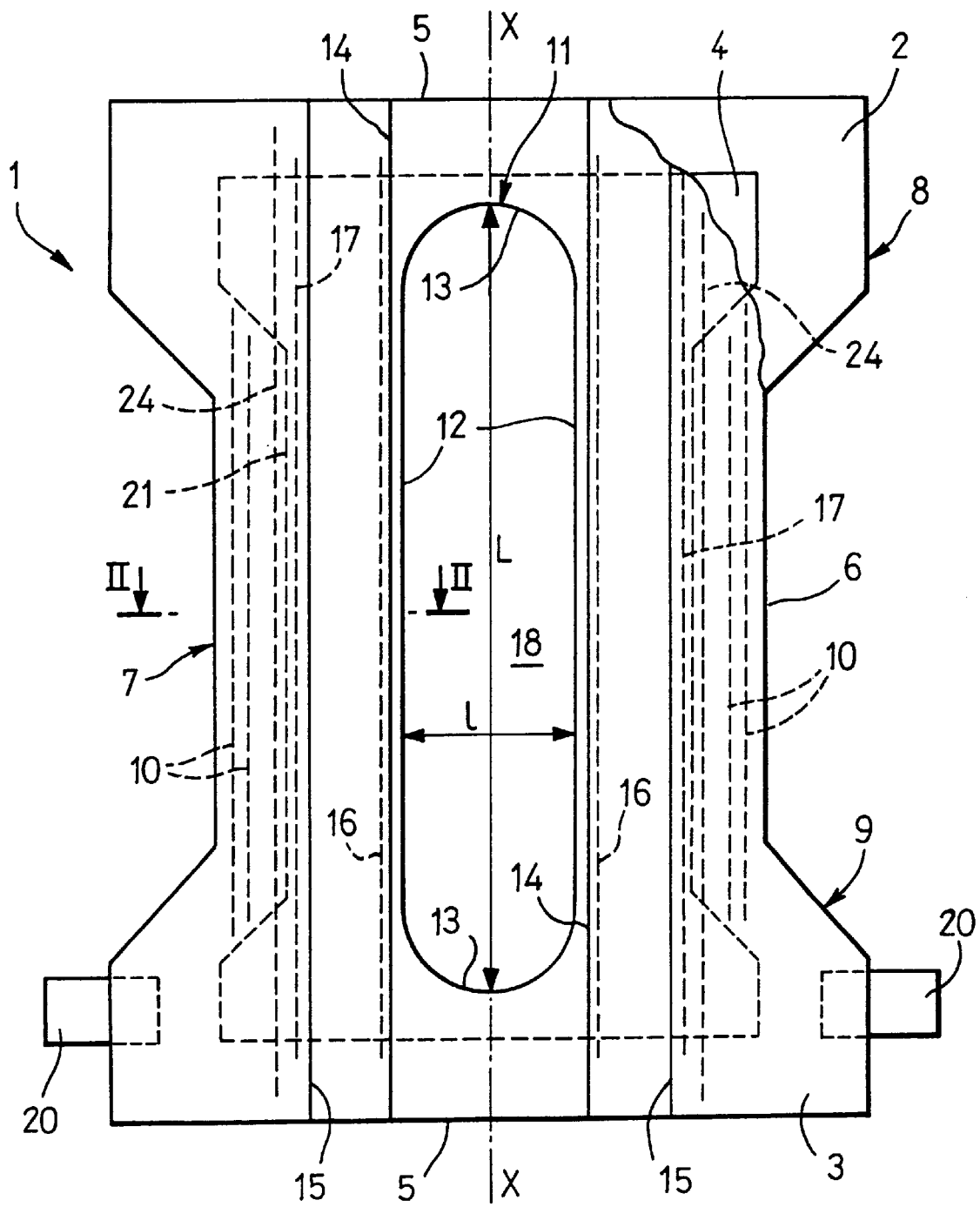
FIG. 1 shows a plan view of the diaper in a stretched condition, with portions cutaway for clarity.

The diaper 1, illustrated in FIG. 1 is composed, in manner known from document U.S. Pat. No. 4,662,877, of an external backing sheet 2 impervious to liquids, such as, for example, a polyethylene film, an internal covering sheet 3, permeable to liquids, such as, for example, a sheet of hydrophobic non-woven, and an absorbent pad 4 placed between said two sheets 2 and 3.

The external backing sheet 2 and the internal covering sheet 3 are of the same dimension and general shape, being substantially of hour-glass shape with two opposite rectilinear transverse edges 5 and two opposite longitudinal edges each one having an indentation 6 defining a crotch area 7 of reduced width and front 8 and rear 9 portions. When the diaper is worn, the crotch area 7, front portion 8 and rear portion 9 will correspond to the zones of the diaper 1 as positioned and fixed around the wearer's waist, by means of the adhesive straps 20.

The absorbent pad 4 is made, for example, of cellulose fluff pulp, optionally containing a highly absorbent polymer. In the illustrated example it has the shape of an hour-glass, similar to the shape of the backing sheet 2 and the internal covering sheet 3. Moreover, it is bonded to the backing sheet 2, symmetrically with respect to the axis XX of symmetry of the diaper 1.

The diaper 1 further comprises elastic elements 10 in the crotch area, which elastic elements are fixed between the backing sheet 2 and the covering sheet 3 longitudinally along each one of the external edges of the diaper 1 in the crotch area 7, as shown in FIG. 1 in a stretched condition.

The internal covering sheet 3 is provided with a central opening 11 defined by two rectilinear longitudinal edges 12 and two transverse edges 13, which are shown as semicircular edges in FIG. 1. Said central opening 11 extends symmetrically with respect to axis XX, in the longitudinal direction of the diaper 1, over the absorbent pad 4, through a length L which is greater than the crotch area 7. The width l of the central opening 11, between the two longitudinal edges 12, is, for example, about half of the width of the absorbent pad 4 in the crotch area 7.

Figure 2:
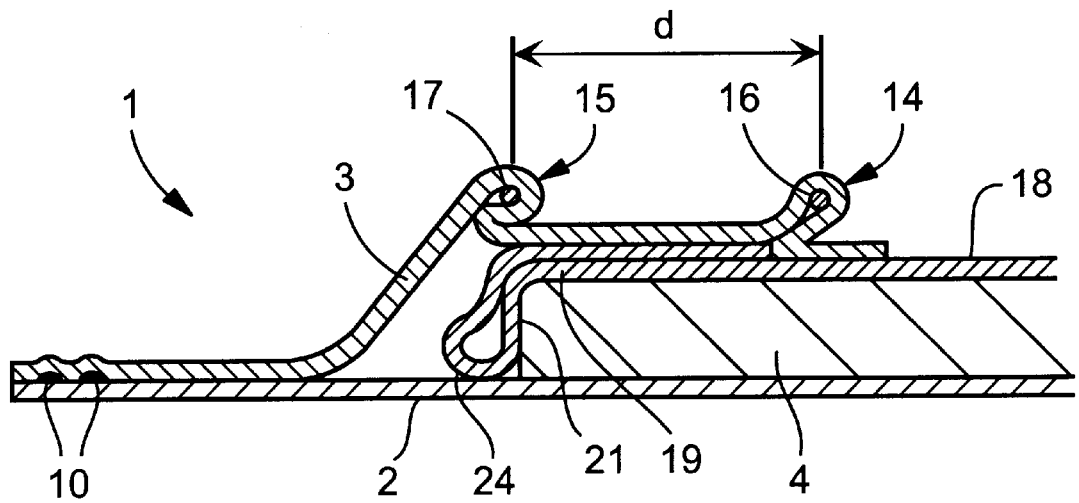
FIG. 2 is a half-view in cross-section along line II—II of FIG. 1.
Figure 3:
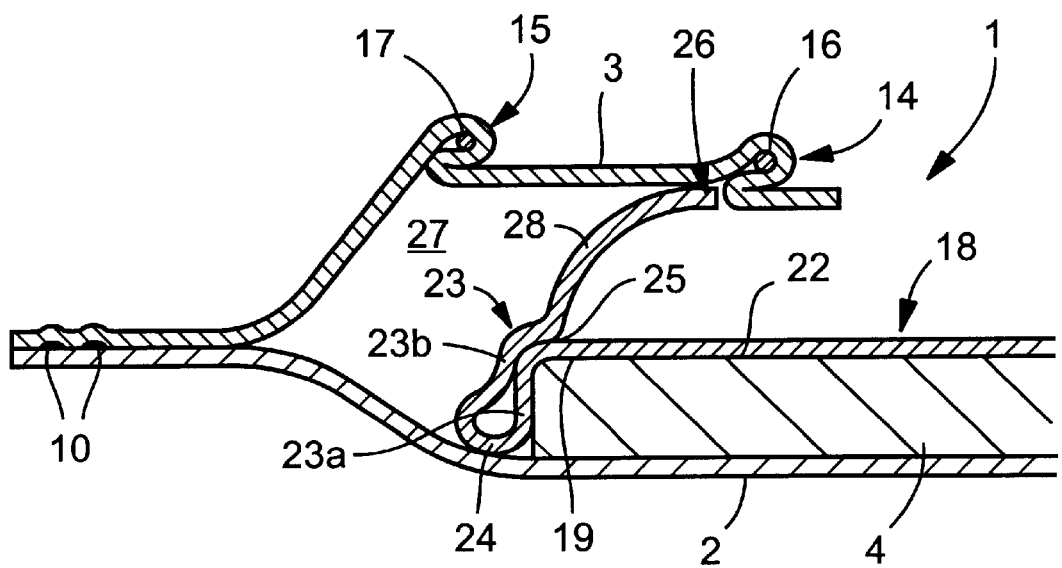
FIG. 3 shows the diaper of FIG. 2 in a non-stretched condition.

As clearly seen when examining FIGS. 2 and 3, the internal covering sheet 3 is provided symmetrically with respect to axis XX, on each side of the central opening 11 with a set of two Z-shaped longitudinal folds 14, 15. Elastic elements 16, 17 are fixed, for example, by bonding within the longitudinal folds. Said elastic elements 16, 17 are fixed in a stretched condition within and joined throughout their length to the folds 14, 15, respectively, of said covering sheet 3. However, the method of fixing the elastic elements 16, 17 on the internal covering sheet 3 in the Z-shaped folds is not restrictive. Any other fixing method could be used, notably in S-shaped folds or by direct fixing without fold.

The respective arrangement of the folds 14 and 15 is as follows. The first fold 14 and the corresponding elastic element 16 are placed in the immediate vicinity of a longitudinal edge 12 of the central opening 11. The second fold 15 and the corresponding elastic element 17 are placed at a predetermined distance d from the first fold 14 and from its elastic element 16. In the illustrated example, said distance d is substantially equal to the distance separating the crotch elastic elements 10 and the second elastic element 17.

Moreover, the second elastic element 17 is fixed inside fold 15 in a stretched condition, stretching of said second elastic element 17 being about 20% more than the stretching of the first elastic element 16 when the first elastic element 16 is fixed in a stretched condition inside first fold 14. Comparatively, the crotch elastic elements 10 are, when in the stretched condition, stretched to a greater extent than the second elastic element 17.

The diaper 1 according to the invention further comprises a protection sheet 18, consisting for example, of a non-woven material of rectangular shape.

Said protection sheet 18 is placed between the internal covering sheet 3 and the absorbent pad 4; more specifically, protection sheet 18 covers the absorbent pad 4, to which it is fixed along longitudinal fixing lines, among which at least one pad fixing line 19 is situated on the top of the absorbent pad 4 along its external edge 21. The protection sheet 18 has a width which is greater than that of the absorbent pad. Moreover, while the central strip 22 of said protection sheet 18 which is situated plumb with the absorbent pad 4 is hydrophilic, the two lateral strips 23 extending beyond said central strip 22, from either side of the pad fixing lines 19, are hydrophobic. Each of the lateral strips 23 forms a flap and has two longitudinal edges which are fixed, one of them close to the longitudinal edge of the absorbent pad 4 at least in the crotch area 7 and the other edge 26 on the lower face of the covering sheet 3, close to the second elastic element 16. The hydrophobic nature, and even the imperviousness to liquid, can be obtained, for example, by prior treatment of the protection sheet 18. Each one of the lateral strips 23 is folded over itself, along a longitudinal folding line 24 which is fixed to the backing sheet 2 along the absorbent pad 4 on the outside thereof, at least in the crotch area 7. Moreover, the two sides 23*a* and 23*b* of the lateral strip 23 are fixed together along a flat fixing line 25 which is level with the pad fixing line 19 of the protection sheet 18 on the absorbent pad 4 and extends throughout the length thereof.

Finally, each one of the longitudinal edges 26 of the lateral strips 23 is fixed on the lower face of the covering sheet 3 close to the first elastic element 16.

The protection sheet 18 has the same length as the backing sheet 2 and the internal covering sheet 3. The transverse edges of the protection sheet 18 are assembled, notably by bonding, to the corresponding edges of the backing sheet 2 and of the covering sheet 3.

The preferred embodiment just described exhibits all the advantages brought by the invention. The presence of the longitudinal flaps, each one of which is constituted by the portion 28 of the lateral strip 23 which extends from the flap fixing line 25 to the longitudinal edge 26 fixed to the lower face of the covering sheet 3 enables the creation of a tight pouch situated above the absorbent pad 4. Said pouch forms with the covering sheet 3 a continuous double barrier for preventing the leaks of urine and faeces.

The presence of the third set of elastic elements 17 on the internal covering sheet 3 provides longitudinal tunnels 27 along the longitudinal edges of the absorbent pad 4 and which constitute absorbent side reservoirs for the urine in case the longitudinal flaps are insufficient. These same tunnels may also constitute ventilation tunnels permitting a gaseous exchange, hence a relative reduction of the humidity prevailing in the inside pouch, when the material constituting the hydrophobic flaps is permeable to gases.

Folding over the lateral strip 23 to form the longitudinal flaps provides an additional element of tightness at the level of the absorbent pad 4 since three successive layers of hydrophobic material are thus provided between the absorbent pad 4 and the wearer's skin.

It should also be noted that, due to the greater stretching of the elastic elements 17 of the third set than the elastic elements 16 of the second set, a restoring force is exerted on the internal covering sheet 3 such that a greater widening of the tight pouch is obtained in the transverse direction of the diaper 1. Such widening makes it easier to place the diaper on the wearer.

Figure 4:
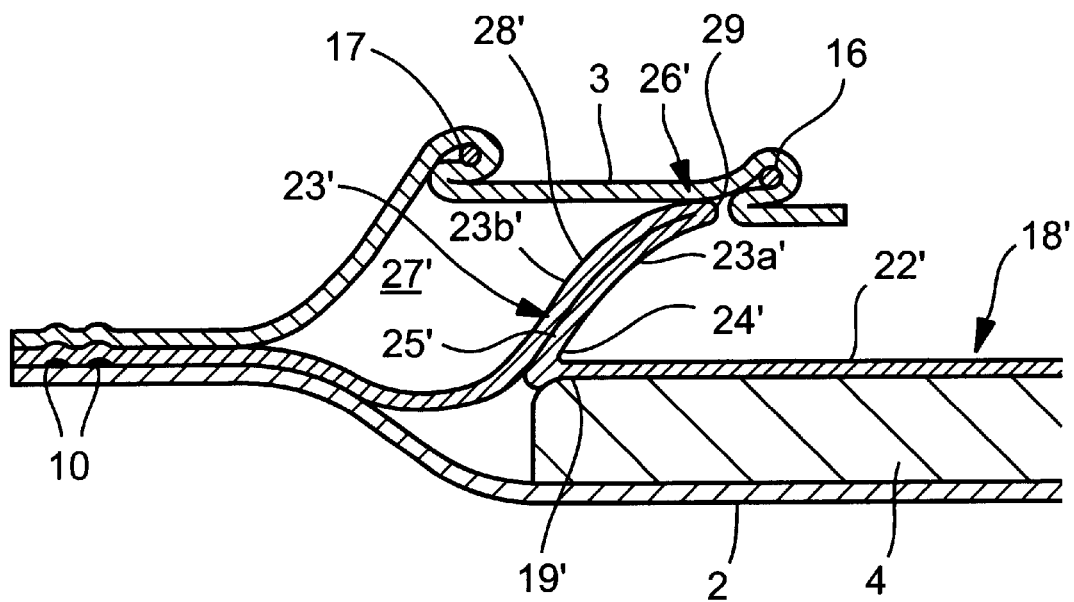
FIG. 4 is a half-view in cross-section, similar to FIG. 3, of a further embodiment of the present invention.

FIG. 4 illustrates another embodiment of the present invention which differs from the above described embodiment in that each lateral strip 23' of protection sheet 18' includes a Z-shaped longitudinal fold, each of which is placed along each longitudinal edge of absorbent pad 4, at least in the crotch area 7. These Z-shaped folds constitute the set of flaps 28'. The lowest longitudinal folding line 24' of each of the Z-shaped folds is fixed to the corresponding longitudinal edge of the absorbent pad 4 along a pad fixing line 19' and the two sides of 23a', 23b' each Z-shaped fold are fixed together along flap fixing line 25' at the level and throughout length of the pad fixing line 19'. Moreover, the upper folding line 29 of each of the Z-shaped folds is fixed to the internal covering sheet 3 near the elastic elements 16.

Additionally, in this embodiment, protection sheet 18' extends beyond each of the longitudinal folding lines 24' so as to cover the external backing sheet 2 to which it is fixed along their common periphery. Also, covering sheet 3 covers, at least partially, protection sheet 18' beyond each of the longitudinal folding lines 24' and is fixed to protection sheet 18' along their common periphery.

Thus, an internal covering sheet 3 of reduced width equal to the width of backing sheet 2 in the crotch area can be used, resulting in savings of material.

There are thus obtained hydrophobic flaps 28' having a double thickness, which therefore constitute a barrier particularly efficient to prevent transverse urine leaks.

Protection sheet 18' may be made of a non-woven material comprising an hydrophilic central strip 22' covering the absorbent pad 4 and treated hydrophobic side strips forming the flaps 28'.

Figure 5:
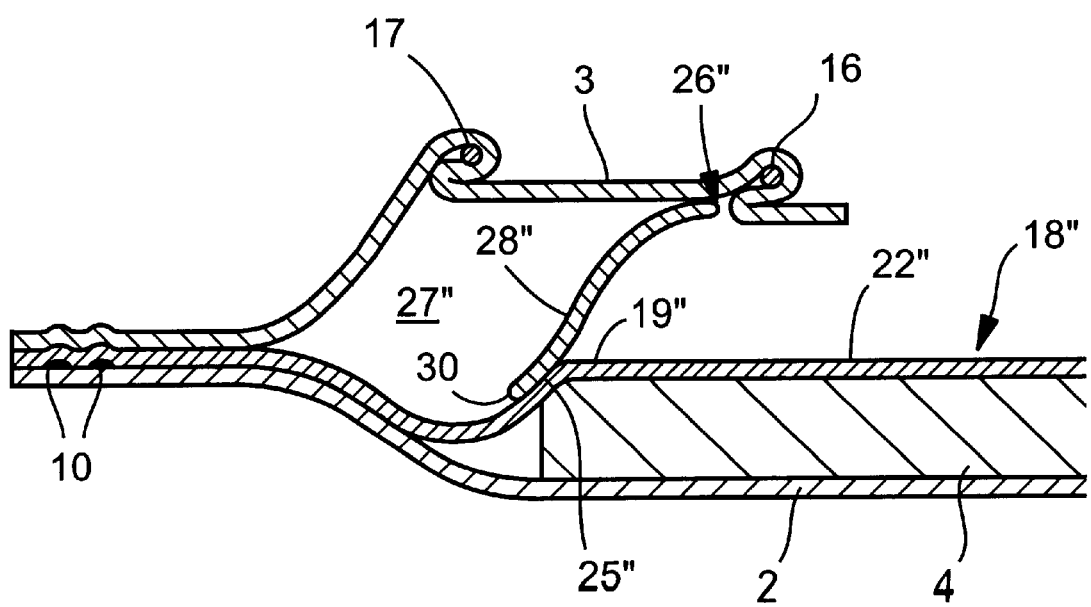
FIG. 5 is a half-view in cross-section, similar to FIG. 3, of still a further embodiment of the present invention.

In still another embodiment illustrated in FIG. 5, protection sheet 18" may be of the same size and of the same substantially hour-glass shape as the external backing sheet 2. Thus, protection sheet 18' extends between the external backing sheet 2 and the internal covering sheet 3 and is fixed to these sheets on their peripheries, for example in the area of the crotch elastic elements 10.

Protection sheet 18' may be made of a non-woven material, which is hydrophilic, or which is hydrophobic, or which is hydrophilic in the central strip thereof covering the absorbent pad 4 and hydrophobic in the adjacent side strips.

Hydrophobic flaps 28" are then formed by separate strips of substantially rectangular shape, made of, for example, a non-woven material, a non-woven material coated with a thermoplastic composition or a thin thermoplastic film in order to be impervious to liquids. The longitudinal edges 30, 26" of the strips are fixed, respectively, on one hand for edge 30, to protection sheet 18" along the longitudinal edges of absorbent pad 4 through a flap fixing line 25", and on the other hand for edge 26", to the covering sheet 3 near the elastic elements 16.

The invention is not limited to the embodiment described hereinabove by way of non-restrictive examples. In particular, the covering sheet 3 could possibly be fixed to the lateral strip 23, for example along two fixing lines which would be situated level with and along the entire length of the fixing line 25 between the two sides 23a and 23b. On the covering sheet 3, said fixing lines would then be situated, symmetrically with respect to axis XX, between the first 10 and the third 17 sets of elastic elements. There would then be, on either side of the absorbent pad 4, two superposed lateral tunnels, of substantially triangular cross-section, having as a common apex the fixing line between the covering sheet 3 and the lateral strip 23.

It is also possible to bring the overlapping zone of covering sheet 3 and of backing sheet 2 substantially closer to the fixing line, and then also the elastic elements 10 of the first set.

What is claimed is:

1. A disposable absorbent sanitary article having:
   a longitudinal axis;
   an absorbent pad having longitudinal edges and placed between a liquid-impervious backing sheet and a hydrophobic internal covering sheet both having longitudinal edges and defining a respective sheet periphery, said backing sheet and said internal covering sheet being of identical shape and being joined together at least along their respective sheet peripheries and defining in the longitudinal direction a crotch area, a front portion and a rear portion;
   said internal covering sheet having a lower face and comprising a central opening, said central opening being defined within said internal covering sheet by two longitudinal edges and two transverse edges and extending symmetrically with respect to the longitudinal axis, in the longitudinal direction over the absorbent pad;
   a first set of elastic elements disposed, in a stretched condition, symmetrically with respect to the longitudinal axis and fixed to the backing sheet and the covering sheet along the longitudinal edges thereof at least in the crotch area;

a second set of elastic elements fixed, in a stretched condition, to the covering sheet in the immediate vicinity of the longitudinal edges of the central opening;

two flaps arranged symmetrically with respect to the longitudinal axis and each flap made of a lateral strip of hydrophobic material, each flap having a first longitudinal edge fixed along a pad fixing line longitudinally extending proximate to a respective longitudinal edge of the absorbent pad, at least in the crotch area, and a second longitudinal edge fixed to the lower face of the covering sheet proximate to the second set of elastic elements; and a protection sheet covering the absorbent pad, the protection sheet having a width greater than a width of the absorbent pad, at least in the crotch area, and being fixed to the absorbent pad along two longitudinally extending pad fixing lines proximate to the two longitudinal edges of the absorbent pad, said protection sheet including a liquid-permeable central strip between said two longitudinally extending pad fixing lines and two lateral hydrophobic strips extending therefrom, wherein said two lateral hydrophobic strips of said protection sheet define said respective lateral strips of hydrophobic material forming said two flap.

2. Sanitary article according to claim 1, wherein each lateral hydrophobic strip of the protection sheet comprises a longitudinal fold having a corresponding folding line, each lateral hydrophobic strip also comprises two facing sides, each of said folding lines being fixed longitudinally on the impervious backing sheet along the absorbent pad and externally thereto, at least in the crotch area, and the two facing sides of each longitudinal fold are fixed together along a flap fixing line, which is level with and extends throughout a length of the corresponding pad fixing line of the protection sheet to the absorbent pad.

3. Sanitary article according to claim 1, wherein each said lateral hydrophobic strip of the protection sheet comprises a double longitudinal fold having a Z-shape and two facing sides, said longitudinally extending pad fixing lines corresponding to respective lower folding lines of said folds, and the two facing sides of each lateral hydrophobic strip are fixed together along a flap fixing line at a level and throughout a length of the respective longitudinally extending pad fixing line.

4. Sanitary article according to claim 1, wherein the elastic elements of the second set are fixed by bonding, each one in a longitudinal fold formed in the covering sheet.

5. Sanitary article according to claim 1, wherein each said lateral hydrophobic strip is immediately adjacent to the respective longitudinal edge of the absorbent pad.

6. A disposable absorbent sanitary article having:

a longitudinal axis;

an absorbent pad having longitudinal edges and placed between a liquid-impervious backing sheet and a hydrophobic internal covering sheet both having longitudinal edges and defining a respective sheet periphery, said backing sheet and said internal covering sheet being of identical shape and being joined together at least along their respective sheet peripheries and defining in the longitudinal direction a crotch area, a front portion and a rear portion;

said internal covering sheet having a lower face and comprising a central opening, said central opening being defined within said internal covering sheet by two longitudinal edges and two transverse edges and extending symmetrically with respect to the longitudinal axis, in the longitudinal direction over the absorbent pad;

a first set of elastic elements disposed, in a stretched condition, symmetrically with respect to the longitudinal axis and fixed to the backing sheet and the covering sheet along the longitudinal edges thereof at least in the crotch area;

a second set of elastic elements fixed, in a stretched condition, to the covering sheet in the immediate vicinity of the longitudinal edges of the central opening;

two flaps arranged symmetrically with respect to the longitudinal axis and each flap made of a lateral strip of hydrophobic material, each flap having a first longitudinal edge fixed along a pad fixing line longitudinal extending proximate to a respective longitudinal edge of the absorbent pad, at least in the crotch area, and a second longitudinal edge fixed to the lower face of the covering sheet proximate to the second set of elastic elements;

a third set of elastic elements disposed, in a stretched condition, symmetrically with respect to the longitudinal axis and fixed longitudinally to the internal covering sheet between the second longitudinal edges of the flaps fixed to said covering sheet and the first set of elastic elements; and wherein stretching of the elastic elements of the third set is greater than stretching of the elastic elements of the second set, in a stretched condition.

7. A disposable absorbent sanitary article having:

a longitudinal axis;

an absorbent pad having longitudinal edges, a top and a bottom surface, and placed between a liquid-impervious backing sheet and a hydrophobic internal covering sheet both having longitudinal edges and defining a respective sheet periphery, said backing sheet and said internal covering sheet being of identical shape and being joined together at least along their respective sheet peripheries and defining in the longitudinal direction a crotch area, a front portion and a rear portion;

said internal covering sheet having a lower face and comprising a central opening, said central opening being defined within said internal covering sheet by two longitudinal edges and two transverse edges and extending symmetrically with respect to the longitudinal axis, in the longitudinal direction over the absorbent pad;

a first set of elastic elements disposed, in a stretched condition, symmetrically with respect to the longitudinal axis and fixed to the backing sheet and the covering sheet along the longitudinal edges thereof at least in the crotch area;

a second set of elastic elements fixed, in a stretched condition, to the covering sheet in the immediate vicinity of the longitudinal edges of the central opening;

two flaps arranged symmetrically with respect to the longitudinal axis and each flap made of a lateral strip of hydrophobic material, each flap having a first longitudinal edge fixed along a pad fixing line longitudinally extending proximate to a respective longitudinal edge on the top surface of the absorbent pad, at least in the crotch area, and a second longitudinal edge fixed to the lower face of the covering sheet proximate to the second set of elastic elements; and a third set of elastic elements disposed, in a stretched condition, symmetrically with respect to the longitudinal axis and fixed longitudinally to the internal covering sheet between the second longitudinal edges of the flaps fixed to said covering sheet and the first set of elastic elements.

8. Sanitary article corresponding to claim 7, wherein the elastic elements of the third set are disposed at a substantially equal distance from the first and second sets of elastic elements.

9. Sanitary article according to claim 7, wherein stretching of the elastic elements of the third set is greater than stretching of the elastic elements of the second set, in a stretched condition.

10. Sanitary article according to claim 7, wherein the elastic elements of the second and third sets are fixed by bonding, each one in a longitudinal fold formed in the covering sheet.

* * * * *